US008207159B2

(12) United States Patent
Opitz et al.

(10) Patent No.: US 8,207,159 B2
(45) Date of Patent: Jun. 26, 2012

(54) USE OF GALANTHAMINE FOR THE TREATMENT OF PATHOLOGICAL MANIFESTATIONS OF THE CENTRAL NERVOUS SYSTEM BASED ON INTOXICATIONS WITH PSYCHOTROPIC SUBSTANCES

(75) Inventors: Klaus Opitz, Muenster (DE); Joachim Moormann, Werne (DE); Thomas Hille, Neuwied (DE); Frank Becher, Koblenz (DE)

(73) Assignee: HF Arzneimittelforschung GmbH, Werne (DE)

( * ) Notice: Subject to any disclaimer, the term of this patent is extended or adjusted under 35 U.S.C. 154(b) by 118 days.

(21) Appl. No.: 10/475,357

(22) PCT Filed: Apr. 18, 2002

(86) PCT No.: PCT/EP02/04277
§ 371 (c)(1),
(2), (4) Date: Oct. 20, 2003

(87) PCT Pub. No.: WO02/085370
PCT Pub. Date: Oct. 31, 2002

(65) Prior Publication Data
US 2004/0116406 A1 Jun. 17, 2004

(30) Foreign Application Priority Data
Apr. 24, 2001 (DE) .................................. 101 19 862

(51) Int. Cl.
*A61K 31/55* (2006.01)
(52) U.S. Cl. ........................................ 514/215; 514/811
(58) Field of Classification Search ................. 514/215, 514/811
See application file for complete search history.

(56) References Cited

U.S. PATENT DOCUMENTS

| | | | |
|---|---|---|---|
| 3,742,951 A | 7/1973 | Zaffaroni | |
| 3,797,494 A | 3/1974 | Zaffaroni | |
| 3,996,934 A | 12/1976 | Zaffaroni | |
| 4,031,894 A | 6/1977 | Urquhart et al. | |
| 4,666,829 A * | 5/1987 | Glenner et al. | 435/6 |
| 4,769,028 A | 9/1988 | Hoffmann et al. | |
| 5,015,645 A * | 5/1991 | Wasley | 514/250 |
| 5,089,267 A | 2/1992 | Hille et al. | |
| 5,519,017 A | 5/1996 | Opitz | |
| 5,589,475 A | 12/1996 | Snorrason | |
| 5,643,905 A | 7/1997 | Moormann | |
| 5,932,238 A | 8/1999 | Opitz | |
| 5,932,557 A * | 8/1999 | Mustafa et al. | 514/44 |
| 5,965,571 A * | 10/1999 | Hutchinson | 514/297 |
| 6,150,354 A * | 11/2000 | Davis et al. | 514/215 |
| 6,194,404 B1 | 2/2001 | Hille et al. | |
| 2004/0202705 A1 * | 10/2004 | Xiong et al. | 424/449 |
| 2005/0009861 A1 * | 1/2005 | Villalobos et al. | 514/300 |

FOREIGN PATENT DOCUMENTS

| | | |
|---|---|---|
| DE | 1 193 061 | 5/1965 |
| DE | 33 15 272 A1 | 10/1984 |
| DE | 38 43 239 C1 | 2/1990 |
| DE | 40 10 079 A1 | 10/1991 |
| DE | 43 01 782 C1 | 8/1994 |
| DE | 195 09 663 A1 | 9/1996 |
| EP | 0 449 247 A | 10/1991 |
| WO | 92 20328 A | 11/1992 |
| WO | 94 16708 A | 8/1994 |

OTHER PUBLICATIONS

Cummings et al. Evidence for psychotropic effects of acetylcholinesterase inhibitors. CNS Drugs, 2000 vol. 13, No. 6, pp. 385-395.*
Sparadeo et al. Cognitive deficits in alcohol troubled females: A comparative Study. Dissertation Abstracts International, 1981 vol. 43, No. 4B, p. 1269.*
Iliev et al. Effect of the acetylcholinesterase inhbitior galanthamine on learning and memory in prolonged alcohol intake rat model of acetylcholine deficit. Methods and Findings in Experimental and Clinical Pharmacology, May, 1999 vol. 21, No. 4, pp. 297-301.*
Arendt T. Impairment in memory function and neuodegenerative changes in the cholinergic basal forebrain system induced by chronic intake of ethanol. J. Neural Transm. 1994, Suppl. 44: pp. 173-187.*
Stuntz P M et al:Society for Neuroscience Abstracts, vol. 26, No. 1-2, 2000, pp. Abstract, No. 753.11, XP001094738.
Powers J S et al: Journal of Clinical Pharmacology, vol. 21, No. 1, 1981, pp. 57-60, XP000612564.
T. Kametani et al., J. Chem. Soc. C, vol. 6, 1971, pp. 1043-1047.
K. Shimizu et al., Heterocycles, vol. 8, 1977, pp. 277-282.
H.A.M. Mucke, Drugs of Today, vol. 33, No. 4, 1997, pp. 259-264.
J.E. Sweeney et al., Pharmacology Biochemistry & Behavior, vol. 31, No. 1, 1988, pp. 141-147.
J.J. Sramek et al., Exp. Opin. Invest. Drugs, vol. 9, No. 10, 2000, pp. 2393-2402.
Chemical Abstracts, vol. 115, 1991, p. 84, 115: 198335x.

* cited by examiner

*Primary Examiner* — Jennifer M Kim
(74) *Attorney, Agent, or Firm* — Birch, Stewart, Kolasch & Birch, LLP

(57) ABSTRACT

The invention relates to the use of galanthamine, as free base or as acid addition salt, for the treatment of cerebral, central nervous or psychiatric symptoms, defunctionalization manifestations or disorders occurring through intake of psychotropic substances as a consequence of occasional or chronic abuse of addictive substances, intoxicants or medicines, or as side effects of the use, especially repeated or prolonged, as intended of medicaments, or as an effect of use, in particular repeated or prolonged, not as intended of medicaments, or as a result of acute poisoning by psychotropic toxic substances, or as a result of chronic exposure to toxic substances with a psychotropic effect in humans or other vertebrates.

8 Claims, No Drawings

USE OF GALANTHAMINE FOR THE TREATMENT OF PATHOLOGICAL MANIFESTATIONS OF THE CENTRAL NERVOUS SYSTEM BASED ON INTOXICATIONS WITH PSYCHOTROPIC SUBSTANCES

This application is the national phase under 35 U.S.C. §371 of PCT International Application No. PCT/EP 02/04277 which has an International filing date of Apr. 18, 2002, which designated the United States of America.

The invention relates to the use of galanthamine for the treatment of disorders of the central nervous system such as cerebral, central nervous or psychiatric symptoms, defunctionalization manifestations or disorders which occur as a result of unintentional or intentional intake of psychotropic and/or hallucinogenic agents, e.g. environmental poisons, use and abuse of intoxicants or addictive substances, use and abuse of medicines, especially when there is dependence on addictive substances, especially alcohol dependence, in humans or in vertebrates.

Intake of psychotropic substances, including intoxicants, especially alcohol, is well known to lead to symptoms such as perception disturbances, memory loss, impairment of cognitive ability, general loss of control, aggressiveness, impairment of muscular coordination, etc.

If the substance is deliberately taken as intoxicant, such as, for example, heroin, cocaine or as ethyl alcohol-containing beverage, then although such effects are intended by the intoxicant-consuming person, they are also under certain conditions felt to be disadvantageous. An additional factor is that the severity and the duration of these symptoms may vary and is often difficult for the consumer of the intoxicant to estimate beforehand.

Especially when there is chronic dependence and continued abuse of addictive substances there is not only the generally known organic damage but there is also the occurrence of permanent defunctionalization manifestations which impair, for example, cognitive performance, especially memory performance. This may also lead to sporadic or permanent dementing states. There may also be chronic manifestations of the previously mentioned psychiatric symptoms such as, for example, a general loss of control. These chronic sequelae of alcohol abuse—which occur in a similar way in other addictive substance dependences—represent a considerable impediment to successful implementation of detoxification therapies. Thus, it is known that the loss of control caused by chronic alcohol abuse makes abstinence impossible for the person affected by alcoholism. This is the main reason why even detoxified alcoholics are prone to relapses, usually with serious consequences. The principle that "controlled drinking" is impossible for dependent people was derived from this observation.

It is additionally known that there are great individual differences in intoxicant consumption behaviour, which is why, for example, alcoholics are divided into different categories of drinkers.

The problem for certain alcohol consumers is that, after a particular individual threshold dose has been exceeded, there is a rapid general loss of control with the abovementioned adverse side effects. The affected persons are usually unable to recognize in good time that they have reached their individual threshold dose or even their personal risk of relapse. The loss of control brought about thereby, which often leads to further excessive alcohol consumption, is the reason why such people are often referred to as dangerous drinkers. These are frequently people who have already undergone withdrawal therapies and relapse in this way.

It is known that the loss of control caused by chronic abuse of addictive substances, as well as the impairment of memory performance (and even dementia), often has far-reaching consequences for the affected person and for his surroundings, such as, for example, inability to carry on an occupation, inability to organize daily activities, inability to initiate and maintain social contacts and, resulting therefrom, social isolation.

These defunctionalization manifestations, e.g. the impairment of cognitive performance, often persist even after successfully completed withdrawal therapy. Further psychiatric or cerebral disturbances occurring in association with alcohol abuse or abuse of other addictive substances are, for example: perceptual illusions or hallucinations, amnesia, alterations of consciousness, formal cognitive disturbances, memory deficits, delusions, confabulations, disorientation, states of agitation.

The object therefore was to eliminate or at least alleviate the psychiatric symptoms or symptoms with a central nervous causation, occurring as a consequence of chronic abuse of addictive substances, in particular alcohol abuse, in particular the loss of control, loss of cognitive abilities, dementia, etc.

To solve this problem, the invention proposes using the agent galanthamine for the treatment of people suffering from such sequelae of psychotropic substances, also based on dependencies on addictive substances. It is possible by administration of galanthamine to at least partially abolish or reverse the psychiatric or cerebral pathological manifestation caused as a result of chronic alcohol or intoxicant consumption, in particular the loss of cognitive abilities or loss of control occurring, so that the said abilities are gradually recovered. It is thus possible according to the present invention to eliminate or at least alleviate certain chronic symptoms of dependences on addictive substances.

The invention is based on the surprising observation that in animal experiments administration of galanthamine to rats was able to bring about a recovery of cognitive abilities. This restoration did not occur, or occurred only considerably later, in untreated control animals. It was additionally possible to show in clinical studies on chronically dependent alcoholics that galanthamine caused a general improvement in the cognitive performance of the subjects. A further advantage in this connexion is in particular that better control over the addictive behaviour is made possible, so that the risk of relapse is reduced.

Galanthamine (4a,5,9,10,11,12-hexahydro-3-methoxy-11-methyl-6-H-benzofuro-(3a,3,2-ef)-(2)-benzazepin-6-ol) is a tetracyclic alkaloid occurring in certain plants, especially Amaryllidaceea. It can be obtained from these plants by known processes (e.g. as described in DE 195 09 663 A1 or DE patent 1 193 061) or by synthetic routes (e.g. Kametani et al., Chem. Soc. C. 6, 1043-1047 (1971) or Shimizu et al., Heterocycles 8, 277-282 (1977)).

On the basis of its pharmacological properties, galanthamine is included in the group of reversibly acting cholinesterase inhibitors. Galanthamine is used to treat poliomyelitis, Alzheimer's disease and various nervous system disorders, and to treat narrow angle glaucoma. It has also been proposed to use galanthamine to treat nicotine and alcohol dependence (DE 43 01 782 C1, DE 40 10 079 A1), it being said that galanthamine suppresses the addicts' desire for nicotine or alcohol. Use for treating the symptoms or sequelae caused by chronic abuse of intoxicants, especially alcohol, such as loss of control, loss of cognitive abilities etc., has not previously been described.

According to the invention, galanthamine can be used both in the form of its free base and as acid addition salt for the treatment; preferred salts are galanthamine hydrochloride and galanthamine hydrobromide.

Galanthamine is preferably administered in a pharmaceutical preparation which contains the agent in proportions of from 0.1 to 90% by weight, particularly preferably in proportions of from 2 to 20% by weight, in each case calculated as free galanthamine. The galanthamine-containing pharmaceutical preparations used according to the invention may additionally contain excipients, carriers, stabilizers, etc., in the amounts known to the skilled person.

The dose administered each day is preferably in the range from 0.1 to 100 mg, in particular from 10 to 50 mg.

The preparations which are used according to the present invention for administering galanthamine may contain one or more of the following additives:
- antioxidants, synergists, stabilizers;
- preservatives;
- taste masking agents;
- colours;
- solvents, solubilizers;
- surfactants (emulsifiers, solubilizers, wetting agents, antifoams);
- agents affecting the viscosity and consistency, gel formers;
- absorption promoters;
- adsorbents, humectants, glidants;
- agents affecting disintegration and dissolution, fillers (extenders), peptizers;
- release-delaying agents.

This list is not definitive; the suitable physiologically acceptable substances are known to the skilled person.

Galanthamine can be administered orally or parenterally. It is possible to use known dosage forms such as tablets, coated tablets or pastilles for oral administration. Also suitable are liquid or semiliquid dosage forms, in which case the agent is in the form of a solution or suspension. Solvents or suspending agents which can be used are water, aqueous media or pharmacologically acceptable oils (vegetable or mineral oils). The galanthamine-containing medicaments are preferably formulated as depot medicaments which are able to deliver this agent to the body in a controlled manner over a prolonged period.

It is also possible according to the invention for galanthamine to be administered by the parenteral route. For this purpose it is particularly advantageous to use transdermal or transmucosal dosage forms for the galanthamine administration according to the invention, in particular adhesive transdermal therapeutic systems (agent plasters). These make it possible to deliver the agent in a controlled manner over a prolonged period via the skin to the patient to be treated.

Such systems normally have an agent-containing, contact adhesive polymer matrix which is covered on the side remote from the skin by an agent-impermeable backing, and whose adhesive, agent-delivering surface is covered before application by a detachable protective layer. The manufacture of such systems and the basic materials and excipients which can be used therefor are known in principle to the skilled person; for example, the assembly of such transdermal therapeutical systems is described in German patents DE 33 15 272 and DE 38 43 239 or in U.S. Pat. Nos. 4,769,028, 5,089,267, 3,742,951, 3,797,494, 3,996,934 and 4,031,894.

It is made possible by the present invention to treat certain concomitant effects or sequelae of occasional or chronic use or abuse of addictive substances, by which means the general wellbeing of these patients is improved and the social reintegration of those chronically harmed by addictive substances is assisted. In addition, the galanthamine treatment proposed according to the invention improves the prospects of success of withdrawal therapies and reduces the risk of relapse. The treatment moreover promotes social reintegration of the persons affected.

The described psychiatric or cerebral disturbances, in particular an impairment of cognitive performance or dementia, may also occur as a result of the intake or the use or abuse of other addictive substances and intoxicants, or as a result of use or abuse of medicines. They may furthermore have been caused by intake or uptake of other agents, e.g. such as environmental poisons (PCB, dioxins, furans, pentachlorophenol, mercury compounds and bromine compounds, amalgam, chlorinated hydrocarbons such as certain solvents).

Besides ethyl alcohol which has already been mentioned, harmful agents also include methanol and other alcohols which may be present for example as impurities in alcoholic beverages.

Addictive substances and intoxicants therefore mean in principle for the purposes of the invention all psychotropic substances, whether solid, liquid, in vapour or gas form, with which pathological manifestations of the type mentioned occur on single, occasional, frequent or chronic use or abuse.

The invention relates in particular to the following psychoactive drugs: neuroleptics, antidepressants, tranquillizers (especially benzodiazepines), antipsychotics, hypnotics, psychostimulants (especially amphetamines, "fashionable drugs" such as, for example ecstasy, speed with unstandardized mixtures of agents), natural psychotropic drugs and substances, and synthetic derivatives thereof (e.g. based on St John's wort, valerian, hops, melissa, lavender, kava-kava, absinthe, thorn apple (*Datura stramonium*), angel's trumpet (*Brugsmania* spp.), deadly nightshade (*Atropa belladonna*), GHB (gamma-hydroxybutyric acid); also tetrahydrocannabinol (THC) and THC-containing intoxicants such as marihuana and hashish, furthermore cocaine, crack, LSD, psilocybin, mescaline, mixtures of substances as in opium and absinthe, morphine and morphine derivatives such as heroin, codeine, methadone, scopolamine and hyoscyamine), and certain organic solvents such as acetone, petrol, ether, toluene, trichloroethylene, trichloromethane, and other gases and gas mixtures which are "sniffed" or inhaled, e.g. nitrous oxide.

Even on use as intended are some of the aforementioned substances which are employed for therapeutic purposes it is possible for the side effects mentioned to occur during medically prescribed therapy, especially on repeated or prolonged administration, e.g. cognitive disturbances, cerebral defunctionalization manifestations, psychiatric symptoms, etc.

The present invention therefore provides for the administration of the agent galanthamine to treat such disorders which have been caused by the use as intended or abuse of the aforementioned substances. The same applies to intoxication by the environmental poisons mentioned.

It is also known that the side effects mentioned can be caused not only by use or abuse of psychotropic substances but also as a result of single, multiple or chronic administration of other medicaments. The use according to the invention of galanthamine therefore also extends to the treatment of symptoms or side effects caused in this way.

Cerebral disturbances or psychiatric symptoms, e.g. memory loss or cognitive disturbances, are also observed in the people affected by acute poisoning (e.g. chemical accidents) and in chronic exposure to poisons (e.g. environmental poisons such as wood preservatives, halogenated biphenyls, dioxins, furans, pentachlorophenol, mercury compounds and bromine compounds, mercury, amalgams, halogenated carbon and hydrocarbon compounds, especially chlorinated hydrocarbons, halogenated biphenyls, tributyltin, chromium (VI)-containing wood preservatives, etc.). The use according to the invention of galanthamine therefore also extends to the treatment of people who have been adversely affected by exposure to poisons in the aforementioned way.

Finally, the present application also proposes the administration of galanthamine in the abovementioned cases to other vertebrates, in particular to mammals, suffering from the symptoms or disturbances described above.

The invention claimed is:

1. A method of treating chronic impairment of muscular coordination, which occurs as chronic sequelae of a circumstance selected from the group consisting of occasional or chronic use or abuse of alcohol, said chronic impairment persisting after successfully completed withdrawal therapy, the method comprising administering galanthamine to a subject which has successfully completed withdrawal therapy and is suffering from chronic impairment of muscle coordination, as a free base or as an acid addition salt, in a dose of from 0.1 to 100 mg per day.

2. The method of claim 1, in which the dose is from 10 to 50 mg per day.

3. The method according to claim 1, wherein galanthamine is administered in a pharmaceutical preparation which contains the galanthamine in a proportion of from 0.1 to 90% by weight, calculated as free galanthamine.

4. The method of claim 3, in which the galanthamine is present at from 2 to 20% by weight of the composition.

5. The method according to claim 3, in which the galanthamine is administered in a pharmaceutical preparation that has a depot effect.

6. The method according to claim 3, in which the composition is administered orally.

7. The method according to claim 3, in which the galanthamine is administered parenterally.

8. The method according to claim 3, in which the galanthamine is administered transdermally.

* * * * *